(12) United States Patent
Schüttler et al.

(10) Patent No.: US 9,174,038 B2
(45) Date of Patent: Nov. 3, 2015

(54) NEURAL ELECTRODE AND METHOD FOR FABRICATING THE SAME

(71) Applicant: CorTec GmbH, Freiburg (DE)

(72) Inventors: Martin Schüttler, Freiburg (DE); Christopher W.D. Dodds, New South Wales (AU); Gregg J. Suaning, New South Wales (AU)

(73) Assignee: Cortec GmbH, Freiburg (DE)

( * ) Notice: Subject to any disclaimer, the term of this patent is extended or adjusted under 35 U.S.C. 154(b) by 94 days.

(21) Appl. No.: 14/053,130

(22) Filed: Oct. 14, 2013

(65) Prior Publication Data

US 2014/0046417 A1 Feb. 13, 2014

Related U.S. Application Data

(63) Continuation of application No. PCT/EP2012/056921, filed on Apr. 16, 2012.

(60) Provisional application No. 61/475,763, filed on Apr. 15, 2011.

(51) Int. Cl.
*A61N 1/05* (2006.01)

(52) U.S. Cl.
CPC ............... *A61N 1/05* (2013.01); *A61N 1/0526* (2013.01); *A61N 1/0551* (2013.01); *Y10T 29/49117* (2015.01)

(58) Field of Classification Search
CPC ..... A61N 1/0543; A61N 1/05; A61N 1/0541; A61N 1/36046; H05K 1/118

USPC ........................................... 607/54, 115, 116
See application file for complete search history.

(56) References Cited

U.S. PATENT DOCUMENTS

| | | | |
|---|---|---|---|
| 7,914,842 B1 | 3/2011 | Greenberg | |
| 8,322,027 B1 * | 12/2012 | Greenberg et al. | ............. 29/829 |
| 2011/0034977 A1 | 2/2011 | Janik | |

FOREIGN PATENT DOCUMENTS

| | | |
|---|---|---|
| WO | 2009003182 A1 | 12/2008 |
| WO | 2011112931 A1 | 9/2011 |

OTHER PUBLICATIONS

International Search Report for corresponding PCT Application PCT/EP2012/056921, mailed Jul. 18, 2012.
Suaning G J et al, "Fabrication of multi-layer, high density microelectrode arrays for neural stimulation and bio-signal recording", Neural Engineering, 2007, pp. 5-8, Piscataway, NJ, USA.

(Continued)

*Primary Examiner* — Rex R Holmes
(74) *Attorney, Agent, or Firm* — Myers Wolin, LLC

(57) ABSTRACT

The invention relates to a neural electrode. It relates in particular to such an electrode which is able to withstand high mechanical forces, and to a method of fabrication of the same. The invention discloses an elastic neural electrode, having at least one planar metal layer which comprises conductive material and which is bilaterally covered by an protective elastomer layer, wherein, for reinforcement of the electrode, an additional reinforcement layer comprising reinforcement material is present between the outermost protective elastomer layers.

11 Claims, 2 Drawing Sheets

(56) References Cited

OTHER PUBLICATIONS

Schuettler M. et al, "Stretchable tracks for laser-machined neural electrode arrays", Proceedings of the 31st Annual International Conference of the IEEE Engineering in Medicine and Biology Society: Engineering the Future of Biomedicine, EMBC, Sep. 3, 2009, pp. 1612-1615.

Henle C et al, "Mechanical characterization of neural electrodes based on PDMS-parylene C-PDMS sandwiched system", Engineering in Medicine and Biology Society, EMBC, 2011 Annual International Conference of the IEEE, Aug. 30, 2011, pp. 640-643.

* cited by examiner

NEURAL ELECTRODE AND METHOD FOR FABRICATING THE SAME

CROSS REFERENCE TO RELATED APPLICATIONS

The present application is a continuation of International Application No. PCT/EP2012/056921, filed on Apr. 16, 2012, which claims priority to U.S. Provisional Patent Application 61/475,763, filed Apr. 15, 2011, the contents of each of which are incorporated herein by reference.

FIELD OF THE INVENTION

The invention relates to a neural electrode. It relates in particular to such an electrode which is able to withstand high mechanical forces, and to a method of fabrication of the same.

BACKGROUND

Cross references are provided to related documents:
Schuettler, M., Stiess, S., King, B., Suaning, G. J.: "Fabrication of Implantable Microelectrode Arrays by Laser-Cutting of Silicone Rubber and Platinum Foil". Journal of Neural Engineering, No. 2, p. 121-128 (2005).
Schuettler, M., Pfau, D., Ordonez, J. S., Henle, C., Woias, P., Stieglitz, T.: "Stretchable Tracks for Laser-Machined Neural Electrode Arrays", Proceedings of the IEEE Engineering in Medicine and Biology Conference, pp. 1612-1615, (2009).
Suaning, G. J., Schuettler, M., Ordonez, J. S., Lovell, N. H.: "Fabrication of Multi-Layer, High Density Micro-Electrode Arrays for Neural Stimulation and Bio-Signal Recording", Proceedings of the IEEE Neural Engineering Conference, pp. 5-8 (2007).

The established and published [Schuettler 2005] process of fabricating neural electrodes based on metalized elastomer is improved in order to allow a better mechanical stability of the electrode arrays.

The current fabrication process utilizes a laser for cutting metal foil in order to generate electrically conducting tracks and contact pads. These tracks and pads are embedded into a silicone elastomer. Since the silicone is very elastic, it cannot protect the delicate metal tracks against strain and other mechanical load as applied, e.g. during implantation surgery.

SUMMARY

Currently, there is no fabrication process for silicone-based implantable neural electrode, which employs an additional layer which function is to set the mechanical properties of the neural electrode and to protect the metal structures.

The current layering (elastomer-metal-elastomer) will be extended by at least one additional layer of high tensile strength polymer. This polymer acts as mechanical protection, e.g. strain relief in order to minimize the force reaching the delicate metal tracks.

It is safer to handle the electrode structure. The risk of damaging the metal tracks during and after implantation are dramatically reduced. Also, if required, the polymer layer can be shaped in a way to locally strengthen (or stiffen) the electrode array, allowing the designer of the electrode to define anisotropic mechanical properties (e.g. very high Young's modulus in direction longitudinal to the metal tracks, low Young's modulus in lateral direction).

BRIEF DESCRIPTION OF THE DRAWINGS

A potential fabrication process, which can be applied for fabricating polymer-reinforced silicone-based neural electrodes is shown in FIG. 1.

Generating anisotropic mechanical properties in an electrode grid by shaping the polymeric reinforcement embedded in the grid elastomer is shown in FIGS. 2A-C.

DETAILED DESCRIPTION OF THE PREFERRED EMBODIMENTS

In the following, several preferred embodiments of the invention are given. Subsequently, the process according to the invention is described.

The foil used to obtain reinforcement has multiple perforations. Through these holes, the two adjacent layers of elastomer touch each other and establish a strong mechanical link between each other and the polymer foil by interlocking.

In order to enhance the robustness of the neural electrodes, polymer-reinforcement can be combined with giving the conductive metal tracks the shape of meanders. Meander-shaped electrodes permit stretching to some degree without being damaged [Schuettler 2009].

In order to enhance mechanical flexibility of the polymer reinforced neural electrode, the polymer foil can be shaped in a way that it only takes up tensile forces in the direction longitudinal to the metal tracks. In contrast, they cannot take up forces in direction lateral to the tracks and also would not affect the flexibility of the elastomer very much (see FIG. 2).

The neural electrodes could be fabricated in multiple alternating layers of elastomer and laser-patterned metal [Suaning 2007]. Depending on the application, one has to decide which layer is to be used for placing the polymeric reinforcement. Some applications require the use of more than one layer of reinforcement.

Some applications require the use of polymeric reinforcement that has some additional functionality, like:
- carrying makers for imaging technology (e.g. radiopaque)
- carrying fluidic channels allowing controlled drug release
- carrying printed information on how to implant the array or on design aspects like labeling of electrode contacts, etc.
- being (partly) made from degradable material, providing mechanical protection only during implantation and during the curing-in process but providing maximal softness for the delicate neural tissue in the long-term use.

Figure 1:
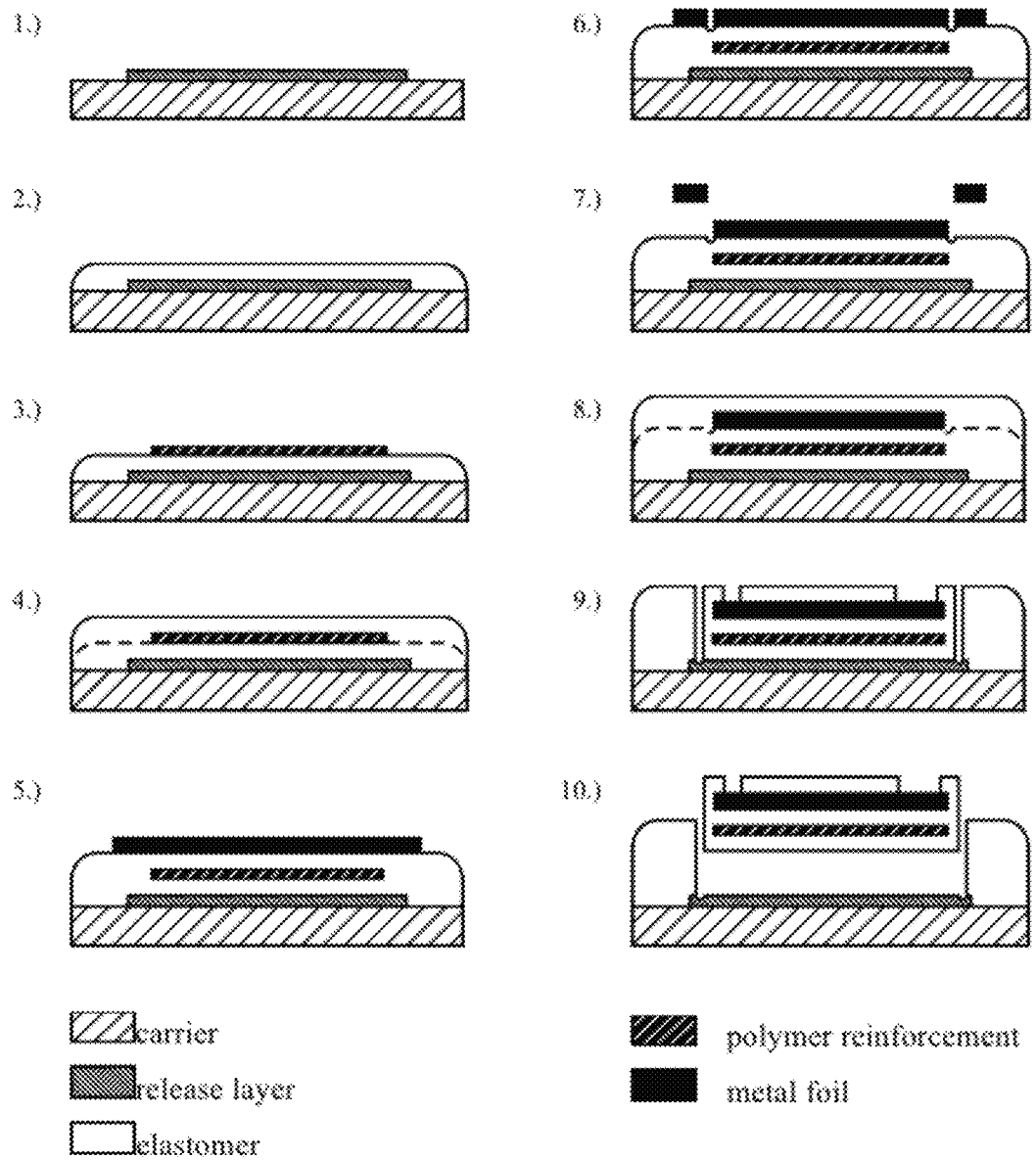

The concept of embedding a polymeric reinforcement in elastomers can be applied but is not restricted to laser-patterning of neural electrodes (as shown in FIG. 1). It is also applicable to photolithography-based patterning of metal layers and/or elastomers, methods based on electroplating of metal on elastomers and other methods employing metal structures embedded in elastomer.

The potential fabrication process, which can be applied for fabricating polymer-reinforced silicone-based neural electrodes, as shown in FIG. 1, requires a mechanical carrier on which the electrode array is processed, which will be discarded after finishing the fabrication. During the first step, a release layer is deposited onto the carrier in order to prevent the uncured elastomer, which is applied in the second step to permanently bond to the carrier. During the third step, the polymeric reinforcement is laminated to the elastomer. Typically, a thin plastic foil is used as reinforcement. This foil will be embedded in elastomer during the next process step.

In step five, a metal foil is laminated onto the elastomer. In the following step, a laser is used to cut the perimeter of contacts and conductive tracks into the metal foil. All metal not needed (e.g. the metal between two adjacent tracks) is manually removed in step seven. A third layer of elastomer is deposited in process set eight, covering the metal tracks. Electrode sites and contact pads are exposed in an additional laser process and the contour of the electrode array is also cut through all elastomer layers using a laser. In step ten, the fabricated electrode array is removed from the mechanical carrier.

Usually, medical grade silicone rubber is used as elastomer. The metal foil could be made from stainless steel, platinum, or similar material. The polymer reinforcement can be made from Polyethylene, Polypropylene, Parylene C, or others.

Figure 2A:
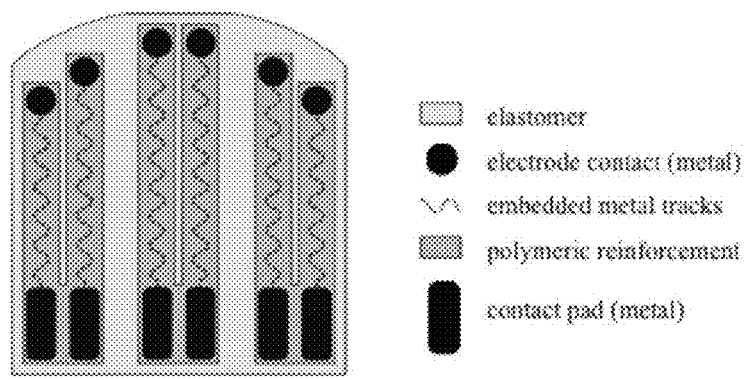

FIG. 2A shows an exemplary design of an electrode according to the invention. More precise, an electrode grid with no forces applied, is shown.

Figure 2B:
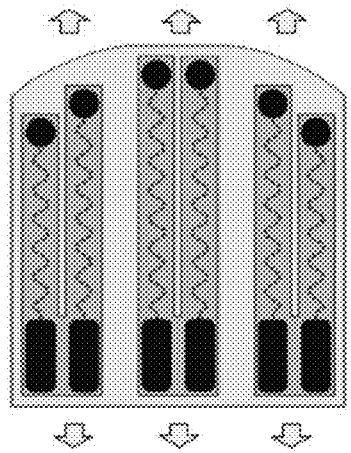

FIG. 2B shows how tensile forces (arrows) in longitudinal direction (relative to the metal tracks) are taken up by the reinforcement and do not affect the shape of electrode grid.

Figure 2C:
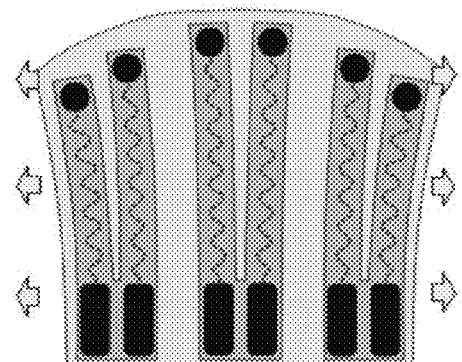

According to FIG. 2C, tensile forces (arrows) in lateral direction (relative to the metal tracks) can affect the shape of the electrode grid without being a risk to the delicate metal tracks.

What is claimed is:

1. An elastic neural electrode, having at least one planar metal layer comprising conductive material and which is bilaterally covered by a protective elastomer layer, wherein, for reinforcement of the electrode, an additional reinforcement layer comprising reinforcement material is present, wherein the electrode comprises a stack of a first protective elastomer layer with openings to the outside, a planar metal layer onto which the openings reach, a second protective elastomer layer, a reinforcement layer, and a third protective elastomer layer.

2. An elastic neural electrode, having at least one planar metal layer comprising conductive material and which is bilaterally covered by a protective elastomer layer, wherein, for reinforcement of the electrode, an additional reinforcement layer comprising reinforcement material is present, wherein the reinforcement layer comprises several parallel arranged and at least partially separated strips of reinforcement material.

3. An elastic neural electrode, having at least one planar metal layer comprising conductive material and which is bilaterally covered by a protective elastomer layer, wherein, for reinforcement of the electrode, an additional reinforcement layer comprising reinforcement material is present, wherein the reinforcement layer has an added functionality comprised of the group consisting of carrying markers for image technology, carrying fluidic channels, and carrying printed information being visible from the outside.

4. An elastic neural electrode, having at least one planar metal layer comprising conductive material and which is bilaterally covered by a protective elastomer layer, wherein, for reinforcement of the electrode, an additional reinforcement layer comprising reinforcement material is present, wherein at least parts of the reinforcement material are degradable.

5. A Method for the fabrication of an elastic neural electrode, having at least one planar metal layer comprising conductive material and which is bilaterally covered by a protective elastomer layer, wherein, for reinforcement of the electrode, an additional reinforcement layer comprising reinforcement material is present, the method comprising at least one of the following steps:
   a) provision of a mechanical carrier;
   b) deposition of a release layer onto the mechanical carrier;
   c) application of a first elastomer layer onto the release carrier;
   d) lamination of a polymer reinforcement layer onto the elastomer;
   e) application of a second elastomer layer onto the polymer reinforcement layer;
   f) lamination of a metal layer onto the second elastomer layer;
   g) shaping the metal layer;
   h) removing unneeded parts of the metal layer;
   i) application of a third elastomer layer onto the metal layer;
   j) partially removing the third elastomer layer for exposure of desired sites of the metal layer;
   k) cutting out the outer contour of the planar electrode; and
   l) removing the electrode from the mechanical carrier.

6. The method of claim 5, wherein the shaping of the metal layer, the removing of unneeded parts of the metal layer, the partial removing the third elastomer, or the cutting out of the outer contour is achieved by means of laser processing.

7. The method of claim 5, wherein the application of metal is achieved by means of photolithography or electroplating.

8. The method of claim 5, wherein the structuring of the elastomer or reinforcement layer is achieved by means of photolithography.

9. The method of claim 5, wherein an additional step of printing information onto the reinforcement layer is carried out.

10. The method of claim 5, wherein an additional step of perforating the reinforcement layer is carried out.

11. The method of claim 5, wherein the steps of lamination of a metal layer, shaping the metal layer, removing unneeded parts of the metal layer and application of an elastomer layer onto the metal layer is carried out more than once.

* * * * *